United States Patent
Pinnau et al.

(10) Patent No.: US 11,746,190 B2
(45) Date of Patent: Sep. 5, 2023

(54) ETHANO-TRÖGER'S BASE-DERIVED DIAMINES, POLYIMIDES, AND POLYIMIDE-BASED MEMBRANES

(71) Applicant: King Abdullah University of Science and Technology, Thuwal (SA)

(72) Inventors: Ingo Pinnau, Thuwal (SA); Bader Ghanem, Thuwal (SA); Yingge Wang, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 17/255,608

(22) PCT Filed: Jul. 16, 2019

(86) PCT No.: PCT/IB2019/056077
§ 371 (c)(1),
(2) Date: Dec. 23, 2020

(87) PCT Pub. No.: WO2020/021389
PCT Pub. Date: Jan. 30, 2020

(65) Prior Publication Data
US 2021/0269598 A1    Sep. 2, 2021

Related U.S. Application Data

(60) Provisional application No. 62/702,141, filed on Jul. 23, 2018.

(51) Int. Cl.
*C08G 73/10* (2006.01)
*B01D 53/22* (2006.01)
(Continued)

(52) U.S. Cl.
CPC ....... *C08G 73/1085* (2013.01); *B01D 53/228* (2013.01); *B01D 71/64* (2013.01); *C07D 487/08* (2013.01)

(58) Field of Classification Search
None
See application file for complete search history.

(56) References Cited

U.S. PATENT DOCUMENTS 9,018,270 B2     4/2015   Mckeown et al.
2010/0269698 A1* 10/2010  Yates ............... B01D 71/64
                                                 96/13

(Continued)

FOREIGN PATENT DOCUMENTS

WO    2017221135 A1    12/2017
WO    WO 2017/221135 A1 * 12/2017 ............. B01D 53/22

OTHER PUBLICATIONS

Michon, Christophe et al., "Stereoselective synthesis of configurationally stable functionalized ethano-bridged Tröger bases", Chem. Commun., 2010, 46, pp. 2206-2208. (Year: 2010).*

(Continued)

*Primary Examiner* — Jason M Greene
(74) *Attorney, Agent, or Firm* — Billion & Armitage

(57) ABSTRACT

Embodiments of the present disclosure generally describe ethano-Tröger's base-amine monomers, ethano-Tröger's base polyimides of intrinsic microporosity, membranes based on ethano-Tröger's base polyimides of intrinsic microporosity, methods of making ethano-Tröger's base-amine monomers, methods of making ethano-Tröger's base polyimides of intrinsic microporosity prepared from ethano-Tröger's base-amine monomers, methods of separating chemical species, and the like.

20 Claims, 3 Drawing Sheets

(51) Int. Cl.
*B01D 71/64* (2006.01)
*C07D 487/08* (2006.01)

(56) References Cited

U.S. PATENT DOCUMENTS

2016/0152630 A1* 6/2016 Ma .................... C08G 73/1085
528/353
2019/0022599 A1* 1/2019 Takeuchi ............... B01D 71/64

OTHER PUBLICATIONS

"Search Report and Written Opinion for PCT/IB2019/056077 dated Nov. 4, 2019".

Kazem-Rostami, "Facile Preparation of ʌ-Shaped Building Blocks: Hunlich Base Derivatization", Synlett, vol. 28, No. 13, Aug. 1, 2017, 1641-1645.

Pereira, et al., "Twisting the ethano-Troger's Base: the bisamide", Organic & Biomolecular Chemistry, vol. 15, No. 3, Jan. 1, 2017, 628-622.

Wang, et al., "Troger's Base-Based Microporous Polyimide Membranes for High-Performance Gas Separation", ACS Macro Letters, vol. 3, No. 7, Jun. 10, 2014, 597-601.

Ghanem, et al., "Novel 6FDA-Based Polyimides Derived from Sterically Hindered Tröger's Base Diamines: Synthesis and Gas Permeation Properties", Polymer, vol. 96, 2016, pp. 13-19.

Hamada, Yasumasa, et al., "Synthesis of ethano-Tröger's base, configurationally stable substitute of Tröger's base", Tetrahedron: Asymmetry, vol. 7, Issue 9, 1996, pp. 2671-2674.

Wang, , et al., "Tröger's base-based copolymers with intrinsic microporosity for CO2 separation and effect of Tröger's base on separation performance", Polym Chem., 2014, 5, 2793.

Zhuang, Yongbing, et al., "Intrinsically Microporous Soluble Polyimides Incorporating Troger's Base for Membrane Gas Separation", Macromolecules, 47, 2014, 3254-3262.

"Communication Pursuant to Article 94(3) EPC dated Dec. 21, 2022", 3 Pages, Application No. 19773172.2.

* cited by examiner

ETHANO-TRÖGER'S BASE-DERIVED DIAMINES, POLYIMIDES, AND POLYIMIDE-BASED MEMBRANES

BACKGROUND

Membrane-based gas separation is an important process for different industrial applications including air separations ($O_2/N_2$), efficient hydrogen recovery ($H_2/N_2$ and $H_2/CH_4$), natural gas sweetening ($CO_2/CH_4$, $H_2S/CH_4$), and carbon capture from flue gas ($CO_2/N_2$). Accordingly, there is an increased demand for the generation of new high performance materials with high permeability and selectivity to decrease the cost of the membranes separation processes. Polymers of Intrinsic Microporosity (PIMs) are among these materials, which, due to their high rigidity and contorted molecular structure, show great potential for different applications including membrane-based gas separation technology. High-performance polyimides of intrinsic microporosity (PIM-PIs) with different contortion centers, such as spirobisindane, ethanoanthracene, triptycene, and Tröger's base are a class of PIMs that show good potential for a wide range of applications, including gas separations. Consequently, for a better understanding of the effect of structural diversity and to enhance the gas separation performance of these materials, there is an increased demand for the design of new building blocks to generate new high-performance PIM-PIs.

Accordingly, it would be desirable to provide an efficient and general approach for the synthesis of high-performance PIM-PIs.

SUMMARY

In general, embodiments of the present disclosure describe ethano-Tröger's base-amine monomers, ethano-Tröger's base polyimides of intrinsic microporosity, membranes including ethano-Tröger's base polyimides of intrinsic microporosity, methods of making ethano-Tröger's base-amine monomers, methods of making ethano-Tröger's base polyimides of intrinsic microporosity, methods of separating chemical species, and the like.

Embodiments of the present disclosure describe an ethano-Tröger's base-amine monomer comprising an ethano-Tröger's base-diamine monomer characterized by the chemical formula:

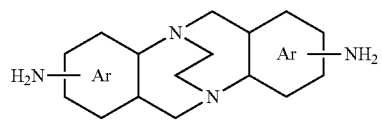

where each Ar is independently one or more of a substituted aryl group and non-substituted aryl group.

Embodiments of the present disclosure describe ethano-Tröger's base polyimides comprising an ethano-Tröger's base polyimide of intrinsic microporosity characterized by the following chemical formula:

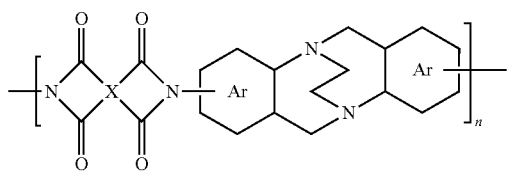

where each Ar is independently one or more of a substituted aryl group and non-substituted aryl group; X is any tetravalent radical having an aromatic and/or aliphatic ring; and n ranges from 2 to 10,000, or more.

Embodiments of the present disclosure describe membranes based on ethano-Tröger's base polyimides of intrinsic microporosity, wherein the geometry of the membranes includes one or more of a flat sheet geometry and hollow fiber geometry.

Embodiments of the present disclosure describe methods of separating chemical species comprising contacting a membrane including an ethano-Tröger's base polyimide of intrinsic microporosity, with a fluid composition containing at least two chemical species and separating at least one of the chemical species from the fluid composition.

Embodiments of the present disclosure describe methods of forming ethano-Tröger's base-diamine monomers comprising alkylating a Tröger's base to form a first intermediate compound including an ethano bridge, nitrating the first intermediate compound to form an intermediate nitro compound including one or more nitro groups, and reducing at least one of the one or more nitro groups of the intermediate nitro compound to form an ethano-Tröger's base-amine monomer.

Embodiments of the present disclosure describe methods of making ethano-Tröger's base polyimides of intrinsic microporosity comprising polymerizing an ethano-Tröger's base-amine monomer with an anhydride monomer to form an ethano-Tröger's base polyimide of intrinsic microporosity and optionally precipitating the ethano-Tröger's base polyimide of intrinsic microporosity in a precipitating agent.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which.

DETAILED DESCRIPTION

Figure 1:
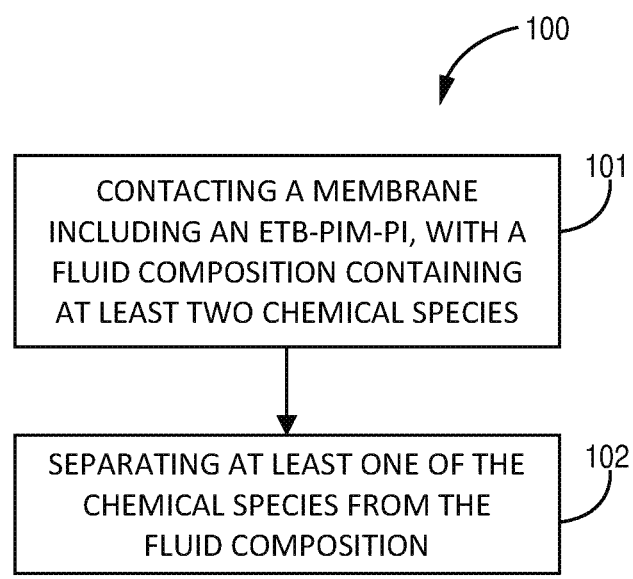
FIG. 1 is a flowchart of a method of separating chemical species, according to one or more embodiments of the present disclosure.

The invention of the present disclosure relates to ethano-Tröger's base-amine monomers, ethano-Tröger's base polyimides of intrinsic microporosity, membranes including ethano-Tröger's base polyimides of intrinsic microporosity, methods of making ethano-Tröger's base-amine monomers, methods of making ethano-Tröger's base polyimides of intrinsic microporosity, methods of separating chemical species, and the like. In particular, the invention of the present disclosure relates to an efficient and general approach for the preparation of ethano-Tröger's base-amine monomers. The methods are general such that the ethano-Tröger's base-amine monomers may be prepared from and/or include any Tröger's base and/or any Tröger's base derivative. For example, a methano bridge of a Tröger's base and/or Tröger's base derivative may be alkylated to form an ethano bridge. After alkylating the Tröger's base and/or Tröger's base derivative, the intermediates may be nitrated and reduced to produce ethano-Tröger's base-amine monomers. The resulting ethano-Tröger's base-amine monomers may include one or more amines. For example, the ethano-Tröger's base-amine monomers may include a diamine (e.g., an ethano-Tröger's base-diamine monomer) and/or a tetraamine (e.g., an ethano-Tröger's base-tetraamine monomer).

The invention of the present disclosure also describes, for the first time, a new class of high performance polyimides of intrinsic microporosity that are prepared from the ethano-Tröger's base-amine monomers of the present disclosure. For example, the polyimides of intrinsic microporosity may include ethano-Tröger's base polyimides of intrinsic microporosity. The ethano-Tröger's base polyimides of intrinsic microporosity may be prepared by polymerizing the ethano-Tröger's base-amine monomers with various anhydride monomers. The methods described herein may be used to fine-tune the microporosity of the polymers to produce materials with high permeability and moderate to high selectivity. The ethano-Tröger's base polyimides of intrinsic microporosity are solution processable (e.g., soluble in common organic solvents), such that the ethano-Tröger's base polyimides of intrinsic microporosity may be used in the fabrication of membranes for a variety of applications, such as fluid separation applications.

The membranes may be prepared in several geometries, such as flat sheet geometry and hollow fiber geometry, and used in a variety of fluid separation applications, such as gas phase separations, liquid phase separations, and mixed-phase separations, among others.

Definitions

The terms recited below have been defined as described below. All other terms and phrases in this disclosure shall be construed according to their ordinary meaning as understood by one of skill in the art.

As used herein, "substituted" refers to all permissible substituents of the compounds described herein. In the broadest sense, the permissible substituents include acyclic and cyclic, branched and unbranched, carbocyclic and heterocyclic, aromatic and nonaromatic substituents of organic compounds. Non-limiting examples of substituents include halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups. Non-limiting examples of substituents (or functional groups, moieties, etc.) include —OH, —F, —Cl, —Br, —I, —NH$_2$, —NO$_2$, —CO$_2$H, —CO$_2$CH$_3$, —CN, —SH, —CH$_3$, —OCH$_3$, —OCH$_2$CH$_3$, —C(O)CH$_3$, —N(CH$_3$)$_2$, —C(O)NH$_2$ or —OC(O)CH$_3$.

As used herein, "ETB" refers to an ethano-Tröger's base. As used herein, "ETBDN" refers to an ethano-Tröger's base dinitro compound. As used herein, "ETBDA" refers to an ethano-Tröger's base-diamine, such as an ethano-Tröger's base-diamine monomer.

As used herein, "Tröger's base" refers to any Tröger's base and/or any derivative thereof. The prototype Tröger's base, 2,8-dimethyl-6H,12H-5,11-methanodibenzo[b,f][1,5]diazocine (CH$_3$C$_6$H$_4$NCH$_2$)$_2$CH$_2$) is a tertiary amine, which exhibits chirality due to the presence of two bridgehead stereogenic nitrogen atoms. It has the general structure:

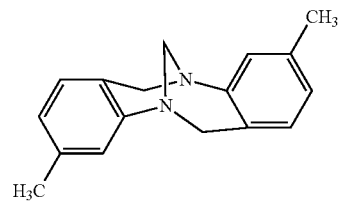 [SMILES: Cc1ccc2c(c1)N1Cc3ccc(C)cc3N(C2)C1]

A Tröger's base derivative may include more functional groups and/or substituents, or less functional groups and/or substituents relative to a Tröger's base on the phenyl rings. The functional groups and/or substituents optionally may be provided at the same or different positions on the phenyl rings relative to the Tröger's base.

As used herein, "ethano Tröger's base" refers to any Tröger's base including a two-carbon bridge and any Tröger's base derivative including a two-carbon bridge. The bridge may be provided in any configuration, such as a Z configuration and/or W configuration. The ethano-Tröger's base derivative of the prototype Tröger's base has the formula (CH$_3$C$_6$H$_4$NCH$_2$)$_2$C$_2$H$_4$).

As used herein, "anhydride" refers to a moiety of the formula R$_1$—C(═O)—O—C(═O)—R$_2$, where R$_1$ and R$_2$ are independently alkyl, haloalkyl, aryl, heteroaryl, cycloalkyl, aromatic alkyl, (cycloalkyl)alkyl and the like.

As used herein, "aromatic" refers to aromaticity, a chemical property in which a conjugated ring of unsaturated bonds, lone pairs, or empty orbitals exhibit a stabilization stronger than would be expected by the stabilization of conjugation alone.

As used herein, "aryl" refers to a monovalent mono-, bi- or tricyclic aromatic hydrocarbon moiety of 6 to 15 ring atoms, which is optionally substituted with one or more, typically one, two, or three substituents within the ring structure or that replace a hydrogen. When two or more substituents are present in an aryl group, each substituent is independently selected. Exemplary aryl includes, but is not limited to, benzene, phenyl, 1-naphthyl, and 2-naphthyl, and the like, each of which can optionally be substituted. The term "aryl" may include heteroaryls or heteroaryl groups.

As used herein, "heteroaryl group" refers to a monovalent mono- or bicyclic aromatic moiety of 5 to 12 ring atoms containing one, two, or three ring heteroatoms selected from N, O, or S, the remaining ring atoms being C. The heteroaryl ring can be optionally substituted with one or more substituents, typically one or two substituents. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

As used herein, "halogen" or "halo" refers to any elements classified as halogens according to the Periodic Table. For example, halogen may include, among others, one or more of fluorine, chlorine, bromine, and iodine. Halo may include, among others, one or more of fluoro, chloro, bromo, and iodo.

As used herein, "alkyl group" refers to a functional group including any alkane with hydrogen removed therefrom. For example, "alkyl" may refer to a saturated linear monovalent hydrocarbon moiety of one to twelve, typically one to six, carbon atoms or a saturated branched monovalent hydrocarbon moiety of three to twelve, typically three to six, carbon atoms. Representative alkyl groups include, but are not limited to, methyl, ethyl, propyl, isopropyl, 1-propyl, 2-propyl, butyl, sec-butyl, isobutyl, tert-butyl, pentyl, hexyl, heptyl, octyl, nonyl, decyl, and the like.

As used herein, the term "alkoxy" or "alkoxy group" refers to a functional group and/or substituent with the chemical formula —OR, where R is any alkyl group. Representative alkoxy groups may include, but are not limited to, one or more of methoxy, ethoxy, propoxy, isopropoxy, butoxy, sec-butoxy, isobutoxy, tert-butoxy, pentoxy, hexoxy, and the like.

As used herein, "aliphatic" refers to organic compounds and/or radicals characterized by substituted or un-substituted straight, branched, and/or cyclic chain arrangements of constituent carbon atoms. Carbon atoms may be joined by single bonds, double bonds, or triple bonds. The term "aliphatic" includes cycloaliphatic compounds/groups and/or alicyclic compounds/groups.

As used herein, "alkylating agent" refers to any compound capable of introducing an alkyl group. An example of an alkylating agent includes, among other things, haloalkanes.

As used herein, "haloalkane" refers to any alkane containing one or more halogens.

As used herein, "contacting" refers to the act of touching, making contact, or of bringing to immediate or close proximity, including at the molecular level, for example, to bring about a chemical reaction, or a physical change, e.g., in a solution, in a reaction mixture. Accordingly, adding, stirring, treating, tumbling, vibrating, shaking, mixing, and applying are forms of contacting to bring two or more components together. In addition or in the alternative, feeding, flowing, passing, injecting, introducing, and/or providing are forms of contacting to bring two or more components together.

As used herein, "alkylating" refers to a process (e.g., chemical reaction) in which the product includes an alkane. For example, the term "alkylating" may include alkylation of a compound with an alkane. An example of alkylating may include direct alkylation, wherein an alkane is used directly as an alkylating agent.

As used herein, "nitrating" refers to a process (e.g., chemical reaction) in which the product includes a nitro group (e.g., —NO$_2$ group). The term "nitrating" may include nitration of a compound with a nitro group.

As used herein, "reducing" refers to a process (e.g., chemical reaction) in which the product includes an amine (—NH$_2$). The term "reducing" may include converting a nitro group to an amine.

As used herein, "separating" refers to the act of removing one or more chemical species from a bulk fluid composition (e.g., gas/vapor, liquid, and/or solid). For example, "separating" may include, but is not limited to, permeating, interacting, bonding, diffusing, adsorbing, absorbing, reacting, and sieving, whether chemically, electronically, electrostatically, physically, or kinetically driven.

Ethano-Tröger's Base-Diamine Monomers

Embodiments of the present disclosure describe ethano-Tröger's base-amine monomers. The ethano-Tröger's base-amine monomers may include one or more amines and/or amine groups. For example, the ethano-Tröger's base-amine monomers may include two amines, forming ethano-Tröger's base-diamine monomers. The ethano-Tröger's base-amine monomers may include four amines, forming ethano-Tröger's base-tetraamine monomers. In many embodiments, the monomers comprise an ethano-Tröger's base-diamine monomer. The ethano-Tröger's base-diamine monomer may be characterized by the following chemical formula:

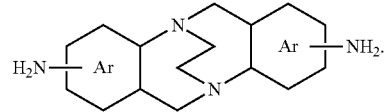

In general, each Ar of the ethano-Tröger's base-amine monomer (e.g., ethano-Tröger's base-diamine and ethano-Tröger's base-tetraamine monomers) may be independently selected. For example, each Ar of the ethano-Tröger's base-amine monomer may be the same (or similar) or different. In many embodiments, each Ar of the ethano-Tröger's base-amine monomer may be the same (or similar). In other embodiments, each Ar of the ethano-Tröger's base-amine monomer may be different.

The Ar may include any aryl group. The aryl group may be one or more of a substituted aryl group and non-substituted aryl group. For example, each Ar of the ethano-Tröger's base-amine monomer may independently be one or more of a substituted aryl group and non-substituted aryl group. In many embodiments, the Ar is an aromatic benzene ring, which may be substituted or non-substituted. For example, each Ar of the ethano-Tröger's base-diamine monomer may independently be one or more of a substituted aromatic benzene ring and non-substituted aromatic benzene ring. The substituted aromatic benzene ring may include one or more functional groups and/or substituents. For example, the substituted aromatic ring may include one or more of hydrogens, halogens, alkyl groups, and alkoxy groups. Examples of suitable halogens may include, among others, one or more of fluorine, chlorine, bromine, and iodine. Examples of suitable alkyl groups may include, among others, one or more of methyl, ethyl, propyl, isopropyl, butyl, and iso-butyl. Examples of suitable alkoxy groups may include, among others, one or more of methoxy, ethoxy, propoxy, butoxy, pentoxy, hexoxy, heptoxy, and octoxy. These shall not be limiting as other substituents disclosed herein can be present or used.

In an embodiment, an ethano-Tröger's base-diamine monomer may be characterized by the following chemical formula:

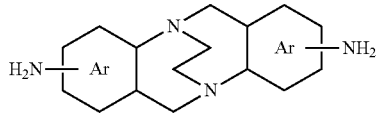

where each Ar is independently one or more of a substituted benzene ring and non-substituted benzene ring. In an embodiment, at least one Ar is a substituted benzene ring including one or more of hydrogen, halogen, alkyl group, and alkoxy group. In an embodiment, the halogen includes one or more of fluorine, bromine, and iodine. In an embodiment, the alkyl group is one or more of cyclic, acyclic, aliphatic, linear, and branched. In an embodiment, the alkyl group includes one or more of methyl, ethyl, propyl, iso-propyl, and iso-butyl. These shall not be limiting as other substituents disclosed herein can be present or used.

In an embodiment, the monomer may include an ethano-Tröger's base-diamine monomer characterized by the following chemical formula:

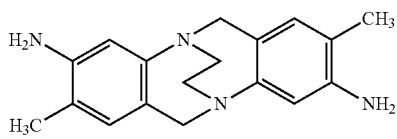

In an embodiment, the monomer may include an ethano-Tröger's base-diamine monomer characterized by the following chemical formula:

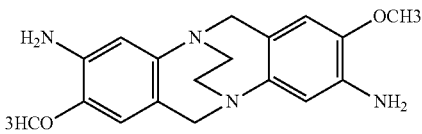

In an embodiment, the monomer may include an ethano-Tröger's base-diamine monomer characterized by the following chemical formula:

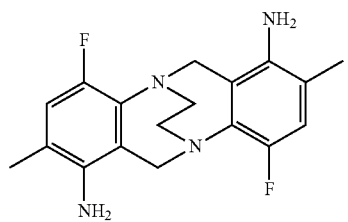

Ethano-Tröger's Base Polyimides of Intrinsic Microporosity (ETB-PIM-PIs)

Embodiments of the present disclosure describe ethano-Tröger's base polyimides of intrinsic microporosity. The polyimides may comprise an ethano-Tröger's base polyimide of intrinsic microporosity characterized by the following chemical formula:

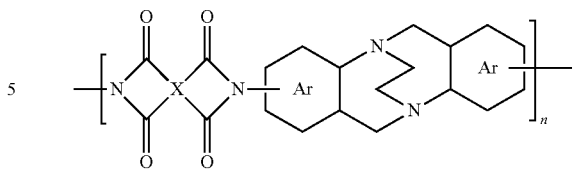

where Ar is an aryl group; X is a tetravalent radical; and n ranges from 2 to 10,000, or more.

In general, each Ar of the ethano-Tröger's base polyimide of intrinsic microporosity may be independently selected. For example, each Ar of the ethano-Tröger's base polyimide of intrinsic microporosity may be the same (or similar) or different. In many embodiments, each Ar of the ethano-Tröger's base polyimide of intrinsic microporosity may be the same (or similar). In other embodiments, each Ar of the ethano-Tröger's base polyimide of intrinsic microporosity may be different. The details of Ar are described above and elsewhere herein, the discussions of which are hereby incorporated by reference in their entirety.

The X may be any tetravalent radical having an aromatic and/or aliphatic ring. In some embodiments, the X may be characterized by one or more of the following chemical structures:

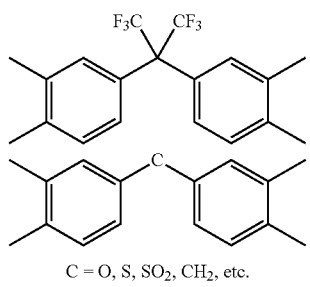

C = O, S, $SO_2$, $CH_2$, etc.

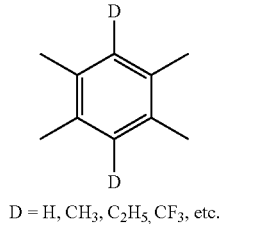

D = H, $CH_3$, $C_2H_5$, $CF_3$, etc.

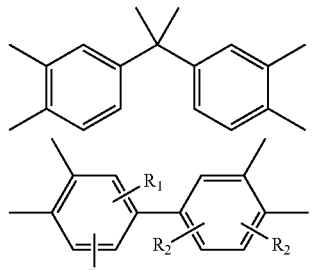

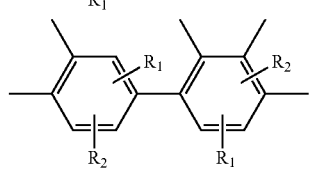

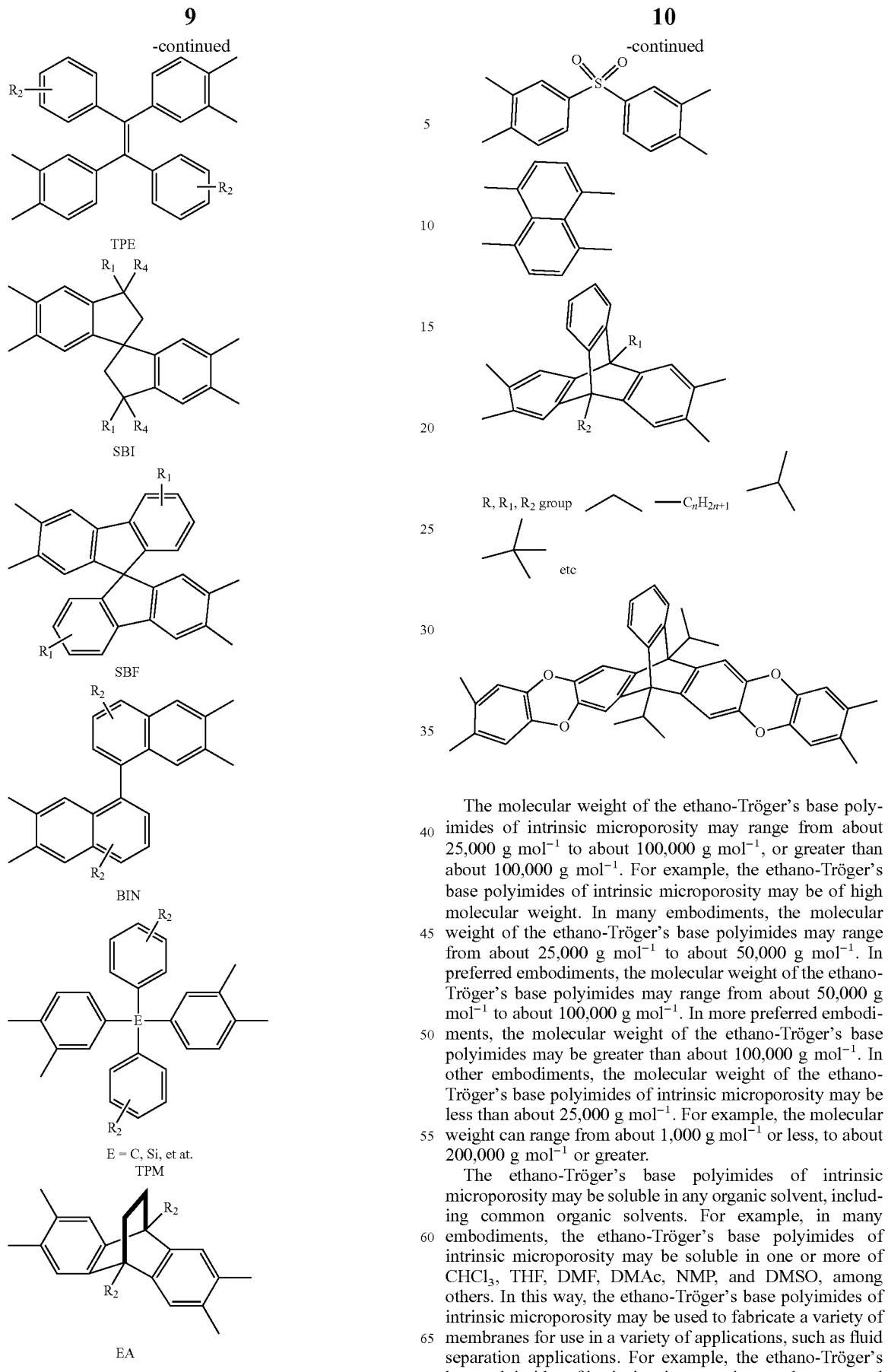

The molecular weight of the ethano-Tröger's base polyimides of intrinsic microporosity may range from about 25,000 g mol$^{-1}$ to about 100,000 g mol$^{-1}$, or greater than about 100,000 g mol$^{-1}$. For example, the ethano-Tröger's base polyimides of intrinsic microporosity may be of high molecular weight. In many embodiments, the molecular weight of the ethano-Tröger's base polyimides may range from about 25,000 g mol$^{-1}$ to about 50,000 g mol$^{-1}$. In preferred embodiments, the molecular weight of the ethano-Tröger's base polyimides may range from about 50,000 g mol$^{-1}$ to about 100,000 g mol$^{-1}$. In more preferred embodiments, the molecular weight of the ethano-Tröger's base polyimides may be greater than about 100,000 g mol$^{-1}$. In other embodiments, the molecular weight of the ethano-Tröger's base polyimides of intrinsic microporosity may be less than about 25,000 g mol$^{-1}$. For example, the molecular weight can range from about 1,000 g mol$^{-1}$ or less, to about 200,000 g mol$^{-1}$ or greater.

The ethano-Tröger's base polyimides of intrinsic microporosity may be soluble in any organic solvent, including common organic solvents. For example, in many embodiments, the ethano-Tröger's base polyimides of intrinsic microporosity may be soluble in one or more of CHCl$_3$, THF, DMF, DMAc, NMP, and DMSO, among others. In this way, the ethano-Tröger's base polyimides of intrinsic microporosity may be used to fabricate a variety of membranes for use in a variety of applications, such as fluid separation applications. For example, the ethano-Tröger's base polyimides of intrinsic microporosity may be contacted with one or more organic solvents and cast to form flexible and mechanically robust films for gas and/or liquid separation applications.

The ethano-Tröger's base polyimides of intrinsic microporosity may exhibit high Brunauer-Emmett-Teller (BET) surface area. For example, in many embodiments, the BET surface area of the ethano-Tröger's base polyimides of intrinsic microporosity may be up to about 400 m$^2$ g$^{-1}$. In other embodiments, the BET surface area of the ethano-Tröger's base polyimides of intrinsic microporosity may be greater than about and/or less than about 400 m$^2$ g$^{-1}$.

In an embodiment, the ethano-Tröger's base microporous polyimide may be characterized by the following chemical structure:

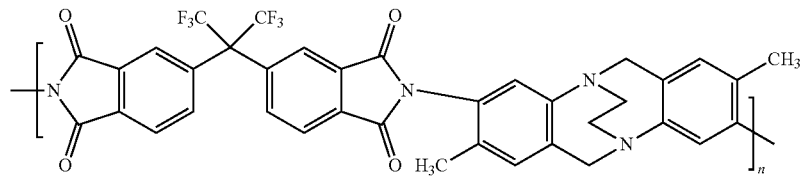

In an embodiment, the ethano-Tröger's base microporous polyimide may be characterized by the following chemical structure:

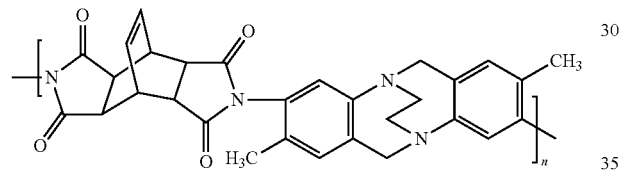

In an embodiment, the ethano-Tröger's base microporous polyimide may be characterized by the following chemical structure:

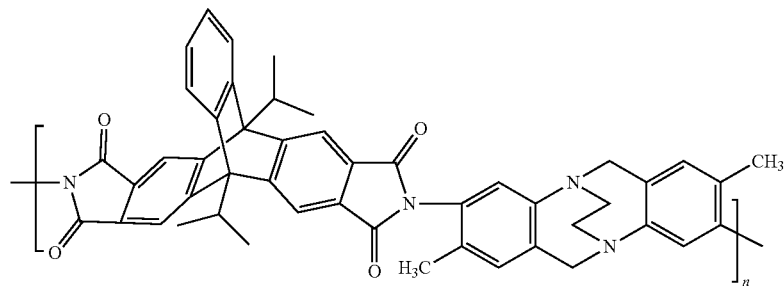

In an embodiment, the ethano-Tröger's base microporous polyimide may be characterized by the following chemical structure:

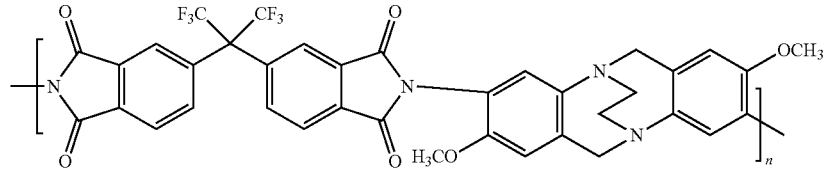

In an embodiment, the ethano-Tröger's base microporous polyimide may be characterized by the following chemical structure:

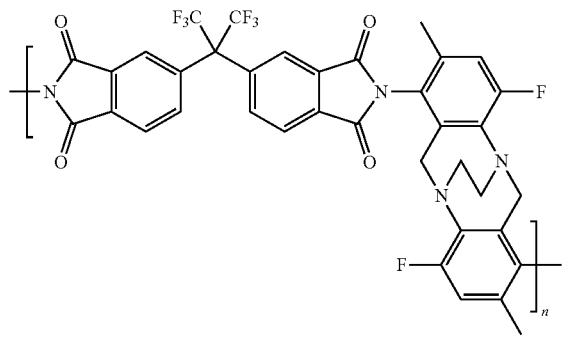

Membranes Based on Ethano-Tröger's Base Polyimides of Intrinsic Microporosity

Embodiments of the present disclosure describe membranes comprising ethano-Tröger's base polyimides of intrinsic microporosity. For example, the membranes may include and/or prepared from any of the ethano-Tröger's base polyimides of intrinsic microporosity and any of the ethano-Tröger's base-amine monomers described herein, the discussion of which is hereby incorporated by reference in its entirety.

The ethano-Tröger's base polyimides of intrinsic microporosity may be used to fabricate membranes, such as thin film composite membranes and/or asymmetric membranes, according to processes and/or methods known in the art. For example, membranes may be fabricated by applying a dilute polymer solution containing the ethano-Tröger's base polyimides onto a support to form a polyimide coating on a microporous substrate in one step by solvent evaporation. In another example, membranes may be fabricated by one or more of phase separation and phase inversion processes.

In many embodiments, the membranes may be provided in a variety of geometries, such as flat sheet geometry and a hollow fiber (e.g., cylindrical) geometry.

Separation of Chemical Species Present in a Fluid Composition

FIG. 1 is a flowchart of a method of separating chemical species, according to one or more embodiments of the present disclosure. As shown in FIG. 1, the method may comprise contacting 101 a membrane including an ethano-Tröger's base polyimide of intrinsic microporosity, with a fluid composition containing at least two chemical species and separating 102 at least one of the chemical species from the fluid composition.

The step 101 includes contacting a membrane including an ethano-Tröger's base polyimide of intrinsic microporosity, with a fluid composition containing at least two chemical species. In this step, one or more chemical species of the fluid composition are brought into physical contact with the membrane, wherein the membrane includes an ethano-Tröger's base polyimide of intrinsic microporosity. The contacting may include one or more of feeding, flowing, passing, injecting, introducing, and providing, among other things. For example, the fluid composition may be fed (e.g., as a feed stream) to the membrane sufficient to make contact with the membrane. The contacting may proceed at and/or under any suitable reaction conditions. For example, the temperature, pressure, concentration of chemical species in the fluid composition, and flow rates, among other parameters, may selected and/or adjusted according to a specific application.

The membrane may include any of the ethano-Tröger's base polyimides of intrinsic microporosity of the present disclosure. The ethano-Tröger's base polyimides of intrinsic microporosity and membranes based thereon have been described herein, the discussion of which is hereby incorporated by reference in its entirety. For example, the membrane may include and/or be prepared from an ethano-Tröger's base microporous polyimide of intrinsic microporosity characterized by the following chemical structure:

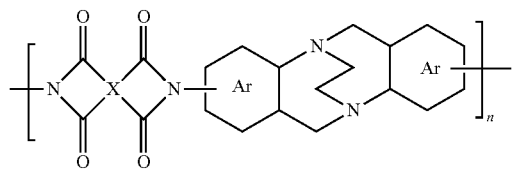

where X is any tetravalent radical having one or more of an aromatic ring and aliphatic ring, where each Ar is independently one or more of a substituted aryl group and non-substituted aryl group, such as a substituted benzene ring and non-substituted benzene ring, and where n ranges from 2 to 10,000, or more.

In an embodiment, the membrane may include an ethano-Tröger's base polyimide characterized by the following chemical structure:

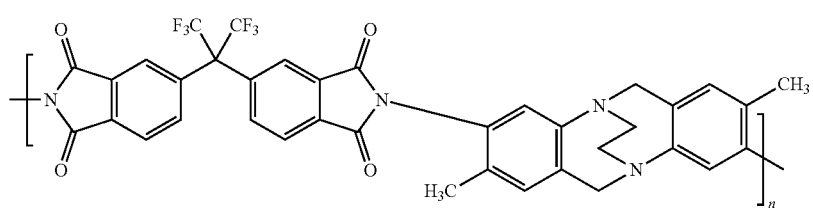

In an embodiment, the membrane may include an ethano-Tröger's base polyimide characterized by the following chemical structure:

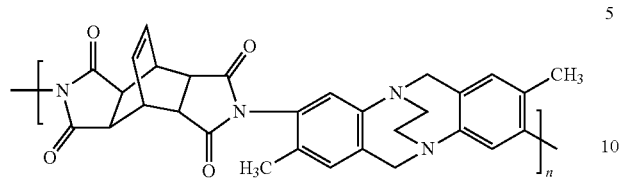

In an embodiment, the membrane may include an ethano-Tröger's base polyimide characterized by the following chemical structure:

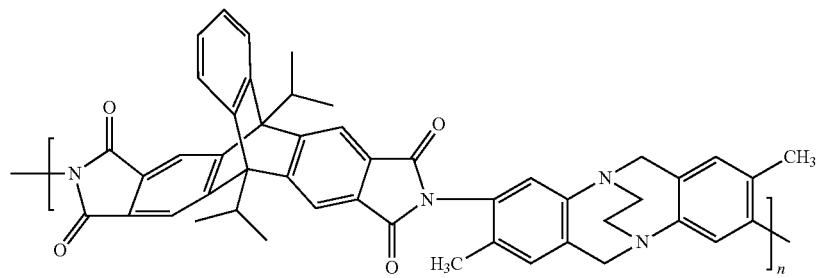

In an embodiment, the membrane may include an ethano-Tröger's base polyimide characterized by the following chemical structure:

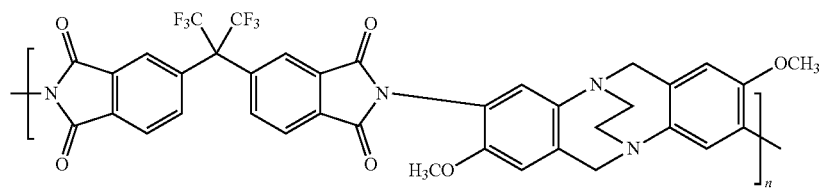

In an embodiment, the membrane may include an ethano-Tröger's base polyimide characterized by the following chemical structure:

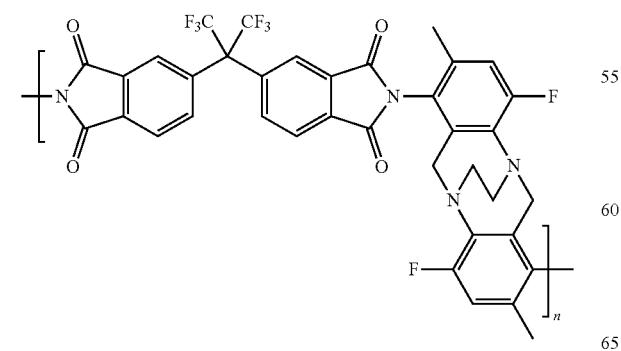

The fluid composition may be provided in any phase or combination of phases. For example, the fluid composition may be provided as one or more of a liquid, vapor, and gas. The fluid composition may include one or more chemical species, such as two or more, three or more, or four or more chemical species. The chemical species of the fluid composition may include one or more of $O_2$, $N_2$, $H_2$, He, $CO_2$, $H_2S$, $C_{1+}$ hydrocarbons (e.g., $CH_4$), olefins, paraffins, n-butane, iso-butane, butenes, and xylene isomers. In many embodiments, the chemical species of the fluid composition may include at least one or more of the following pairs of chemical species: $O_2$ and $N_2$, $H_2$ and $N_2$, $H_2$ and $C_{1+}$ hydrocarbons, He and $C_{1+}$ hydrocarbons, $CO_2$ and $C_{1+}$ hydrocarbons ($CO_2/CH_4$), $CO_2$ and $N_2$, $H_2S$ and $C_{1+}$ hydrocarbons, olefins and paraffins, n-butane and iso-butane, n-butane and butenes, xylene isomers, and combinations thereof. In other embodiments, the chemical species of the fluid composition may include any combination of one or more of the chemical species described herein.

The step 102 includes separating at least one of the chemical species from the fluid composition. In this step, at least one of the chemical species present in the fluid composition is separated from one or more of the other chemical species present in the fluid composition. The separating may depend on a number of factors, including, but not limited to, selectivity, diffusivity, permeability, solubility, conditions (e.g., temperature, pressure, and concentration), membrane properties (e.g., pore size), and the methods used to fabricate the membranes. In many embodiments, the separating may be based on, among other things, permeability, such as differences in permeability of one or more chemical species, among other types of separations. For example, the separating may be achieved by selectively permeating one or more chemical species through the membrane while retaining the other chemical species. In other embodiments, the separation may be based on one or more of permeability, diffusion and sorption (e.g., adsorption and/or absorption).

The separating may include one or more of $O_2/N_2$ separations, $CO_2/CH_4$ separations, $CO_2/N_2$ separations, $H_2S/CH_4$, $H_2/N_2$ separations, and $H_2/CH_4$ separations.

Methods of Making Ethano-Tröger's Base-Diamine Monomers

Figure 2:
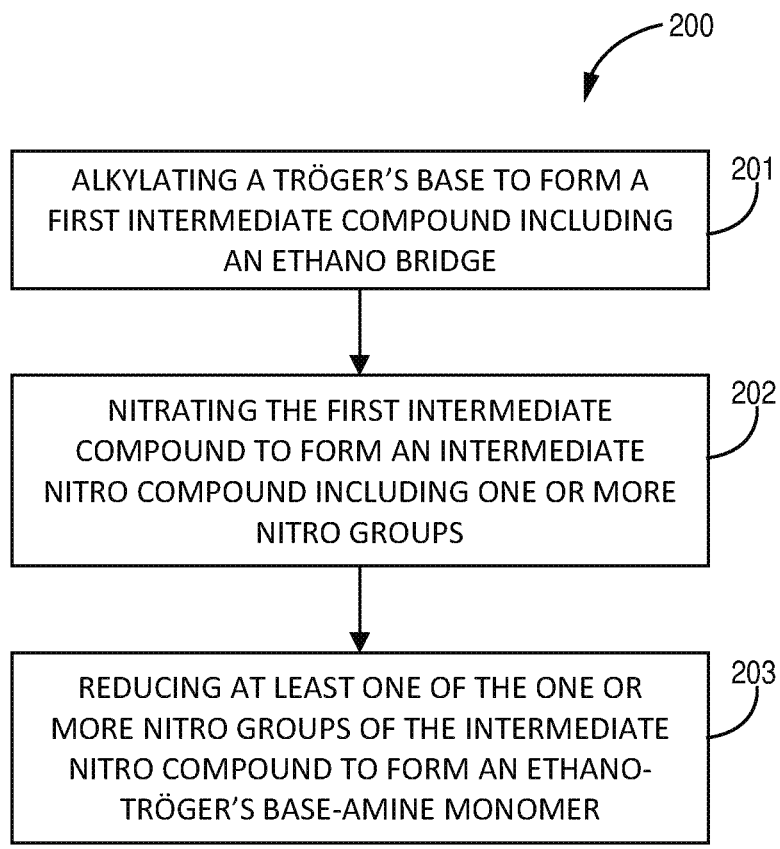
FIG. 2 is a flowchart of a method of making an ethano-Tröger's base-diamine monomer, according to one or more embodiments of the present disclosure.

FIG. 2 is a flowchart of a method of making an ethano-Tröger's base-diamine monomer, according to one or more embodiments of the present disclosure. As shown in FIG. 2, the method may comprise alkylating 201 a Tröger's base to form a first intermediate compound including an ethano bridge, nitrating 202 the first intermediate compound to form an intermediate nitro compound including one or more nitro groups, and reducing 203 at least one of the one or more nitro groups of the intermediate nitro compound to form an ethano-Tröger's base-amine monomer.

The step 201 includes alkylating a Tröger's base to form a first intermediate compound including an ethano bridge. In this step, the alkylating step forms an ethano bridge on the Tröger's base thereby producing the first intermediate compound. For example, the Tröger's base may initially include a methano bridge that may be alkylated to form an ethano bridge on the Tröger's base, thereby producing the first intermediate compound. A non-limiting example of a reaction mechanism illustrating the alkylating of the Tröger's base to form the ethano bridge of the first intermediate compound is provided below in Scheme 1.

Scheme 1

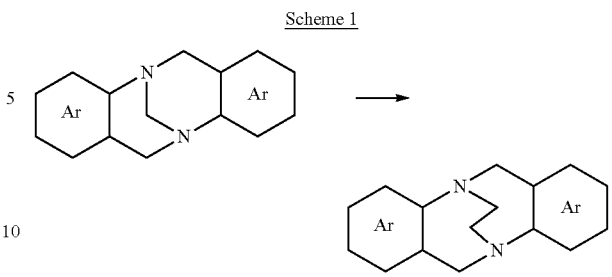

The formation of an ethano bridge upon alkylation of the Tröger's base methano bridge (Scheme 1) provides a novel technique for fine-tuning microporosity to produce a material with improved selectivity.

The alkylating may proceed by any suitable method of alkylation. In many embodiments, the alkylating may proceed by direct alkylation. For example, the alkylating may include contacting, under suitable reaction conditions, one or more of a Tröger's base, alkylating agent, base, and solvent. The Tröger's base may include any of the Tröger's bases of the present disclosure, including, but not limited to, Tröger's bases and/or Tröger's base derivatives. The alkylating agent may include any alkane and/or alkane-based compound suitable for direct alkylation. For example, the alkylating agent may include a haloalkane, such as one or more of fluoroalkanes, bromoalkanes, chloroalkanes, and iodoalkanes. In preferred embodiments, the haloalkane may include an alkane containing two halogens. For example, the haloalkane may include one or more of 1,1-dibromoethane, 1,2-dibromoethane, 1,1-dichloroethane, 1,2-dichloroethane, 1,1-difluoroethane, 1,2-difluoroethane, 1,1-diiodoethane, and 1,2-diiodoethane. The base may include any suitable base. In many embodiments, the base is a strong base. For example, the base may include one or more of lithium carbonate ($Li_2CO_3$), potassium carbonate ($K_2CO_3$), potassium hydroxide (KOH), and sodium hydroxide (NaOH). The solvent may include any suitable organic solvent. For example, the solvent may be polar or non-polar and/or protic or aprotic. In many embodiments, the solvent includes an aprotic solvent, such as one or more of dimethylformamide (DMF), dimethylsulfoxide (DMSO), ethyl acetate, N-methylpyrrolidone (NMP), dimethylacetamide (DMA), and propylene carbonate, among others. While direct alkylation is described herein, in other embodiments, any process and/or technique for alkylating may be used.

The step 202 includes nitrating the first intermediate compound to form an intermediate nitro compound including one or more nitro groups. In this step, the first intermediate compound may undergo reaction sufficient to provide at least one nitro group on the first intermediate compound and form the intermediate nitro compound. In many embodiments, the intermediate nitro compound includes two nitro groups and/or four nitro groups. A non-limiting example of a reaction mechanism illustrating the nitrating of the first intermediate compound to form the intermediate nitro compound is provided below in Scheme 2.

Scheme 2

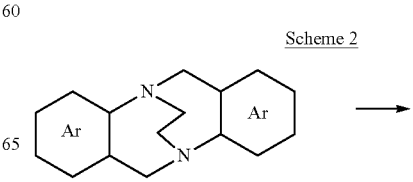

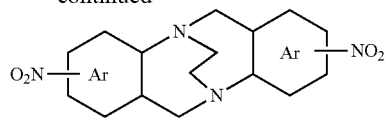
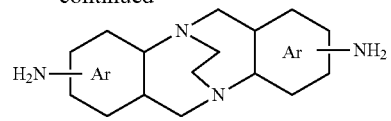

As shown in Scheme 2, the intermediate nitro compound may include two nitro groups, forming, for example, an intermediate dinitro compound. In other embodiments, the second intermediate compound may include four nitro groups, forming a tetranitro compound.

The nitrating may include contacting, under suitable reaction conditions, the first intermediate compound with one or more of potassium nitrate ($KNO_3$), sulfuric acid ($H_2SO_4$), trifluoroacetic anhydride (TFAA), and nitric acid ($HNO_3$) to form the intermediate nitro compound. For example, in many embodiments, the nitrating may include contacting the first intermediate compound with potassium nitrate and one or more of sulfuric acid and trifluoroacetic anhydride. In preferred embodiments, the nitrating may include contacting the first intermediate compound with potassium nitrate and sulfuric acid, such as concentrated sulfuric acid.

The step 203 includes reducing at least one of the one or more nitro groups of the intermediate nitro compound to form an ethano-Tröger's base-amine monomer. In this step, the intermediate nitro compound may undergo reaction sufficient to replace at least one of the one or more nitro groups of the intermediate nitro compound with an amine and produce an ethano-Tröger's base-amine monomer. A non-limiting example of a reaction mechanism illustrating the reducing of the intermediate nitro compound to form the ethano-Tröger's base-diamine monomer is provided below in Scheme 3.

Scheme 3

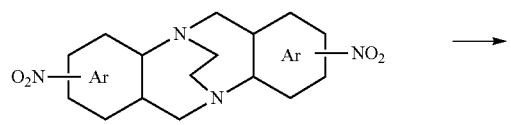

As shown in Scheme 3, the ethano-Tröger's base monomer may include two amine groups, forming, for example, the ethano-Tröger's base-diamine monomer. In other embodiments, the ethano-Tröger's base monomer may include four amines and/or amine groups, forming an ethano-Tröger's base-tetraamine monomer.

The reducing may include replacing at least one of the one or more nitro groups of the intermediate nitro compound with an amine. In embodiments in which the intermediate nitro compound includes one or more nitro groups, one or more of the one or more nitro groups may be reduced such that each of the reduced nitro groups is replaced by an amine. In many embodiments, each of the one or more nitro groups is reduced and replaced by an amine. For example, in an embodiment, the intermediate nitro compound may be provided as an intermediate dinitro compound, wherein each of the two nitro groups of the intermediate dinitro compound is reduced to form an ethano-Tröger's base-diamine monomer. The reducing may proceed by contacting the intermediate nitro compound with and/or in the presence of one or more of hydrazine monohydrate ($N_2H_4 \cdot H_2O$) and palladium carbon (Pd/C) to achieve the amine and/or amines. In many embodiments, the reducing includes replacing each of the two nitro groups of the intermediate dinitro compound with an amine. In other embodiments, the reducing includes replacing each of the four nitro groups of the intermediate tetranitro compound.

In an embodiment, the ethano-Tröger's base-diamine monomer may be prepared according to Scheme 4:

Scheme 4

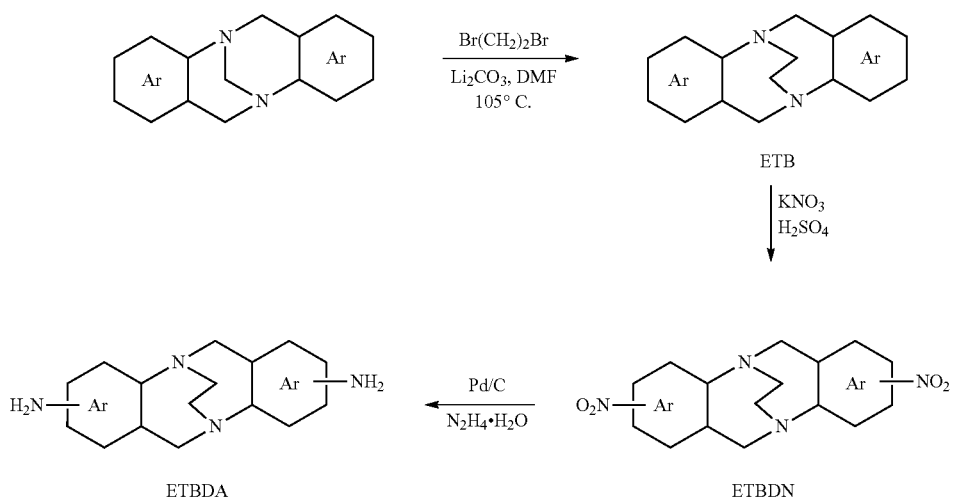

where each Ar is independently a substituted aromatic benzene ring or non-substituted aromatic benzene ring, wherein the substituted aromatic benzene ring may include one or more of hydrogens, halogens, alkyl groups, and alkoxy groups.

In an embodiment, the ethano-Tröger's base-diamine monomer may be prepared according to Scheme 5:

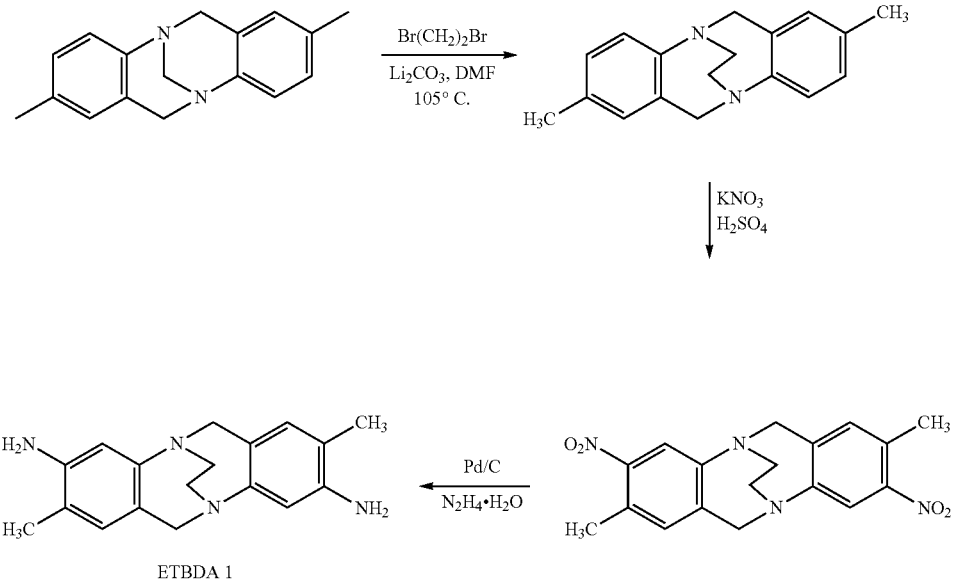

In an embodiment, the ethano-Tröger's base-diamine monomer may be prepared according to Scheme 6:

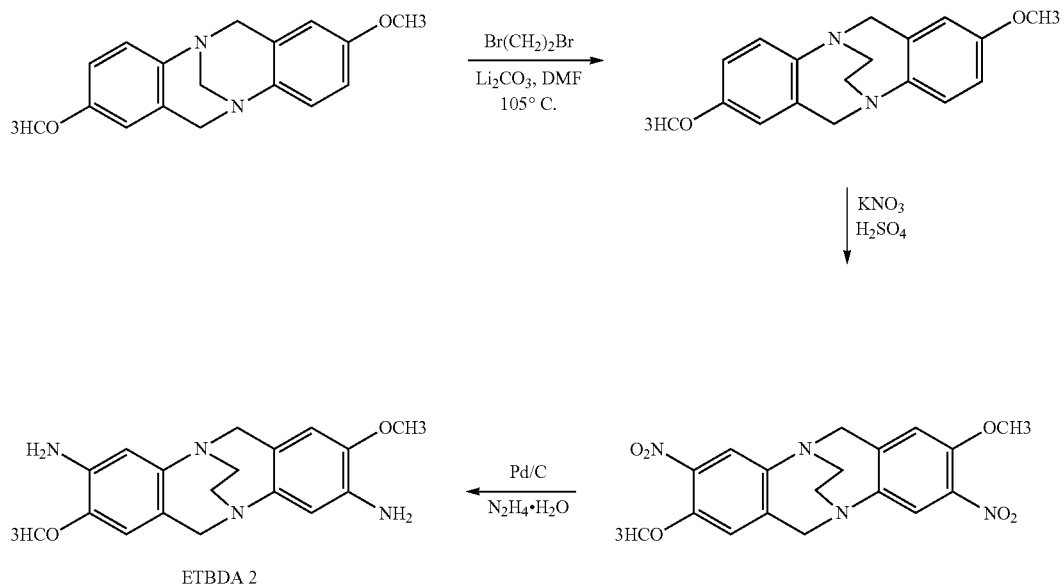

In an embodiment, the ethano-Tröger's base-diamine monomer may be prepared according to Scheme 7:

Scheme 7

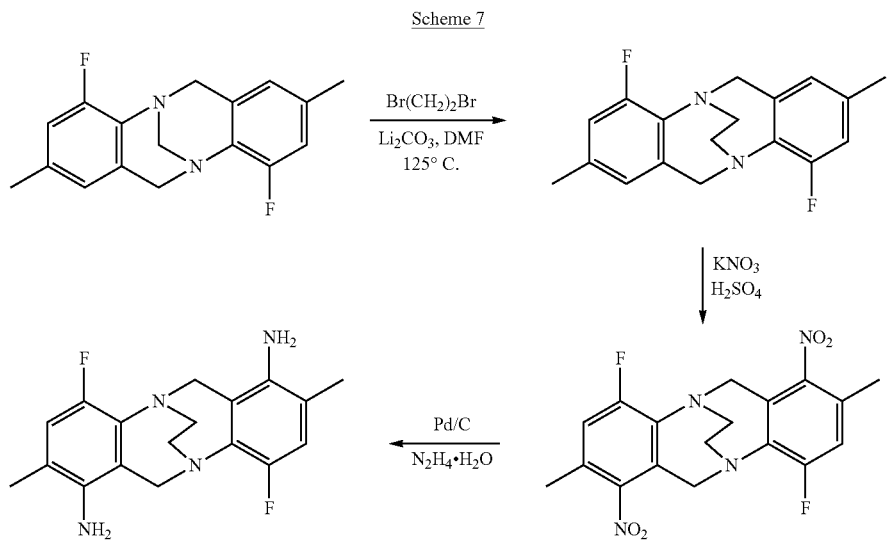

Methods of Making Ethano-Tröger's Base Polyimides of Intrinsic Microporosity

Figure 3:
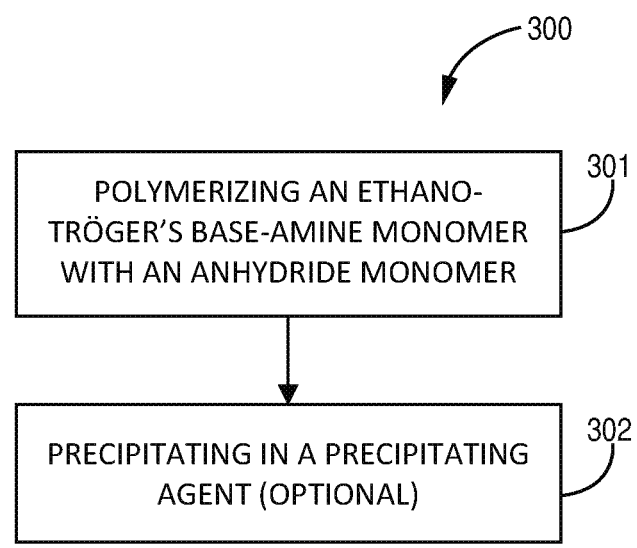
FIG. 3 is a flowchart of a method of making an ethano-Tröger's base polyimide of intrinsic microporosity, according to one or more embodiments of the present disclosure.

FIG. 3 is a flowchart of a method of making an ethano-Tröger's base polyimide of intrinsic microporosity, according to one or more embodiments of the present disclosure. As shown in FIG. 3, the method 300 of making an ethano-Tröger's base polyimide of intrinsic microporosity may comprise polymerizing 301 an ethano-Tröger's base-amine monomer with an anhydride monomer to form an ethano-Tröger's base polyimide of intrinsic microporosity and optionally precipitating 302 the ethano-Tröger's base polyimide of intrinsic microporosity in a precipitating agent.

At step 301, the polymerizing may proceed by a solution imidization method/polycondensation reaction. For example, the polymerizing may include contacting an ethano-Tröger's base-amine monomer with an anhydride monomer in a solution and gradually increasing the temperature. In many embodiments, a 1:1 ratio of the ethano-Tröger's base-amine monomer to anhydride monomer is used. For example, in an embodiment, to achieve high molecular weight polymers, the polymerizing may proceed under precise stoichiometric conditions and/or with compounds of high purity. The temperature of the polymerizing may range from about room temperature to about 200° C. In many embodiments, the temperature may be gradually increased from a first temperature to one or more other temperatures. For example, the polymerizing may proceed at a first temperature and may be subsequently increased to a second temperature. In an embodiment, the first temperature may be about 50° C. and the second temperature may range from about 180° C. to about 200° C. The duration of the reaction may range from about 1 h to about 3. In other embodiments, the duration of the reaction may be less than about 1 h and/or greater than about 3 h. In other embodiments, the polymerizing may proceed according to any other suitable method (e.g., chemical imidization, etc.).

The ethano-Tröger's base-amine monomer may include any of the ethano-Tröger's base-amine monomers described herein, the discussion of which is hereby incorporated by reference in its entirety. In many embodiments, the ethano-Tröger's base-amine monomer is an ethano-Tröger's base-diamine monomer. For example, the ethano-Tröger's base-diamine monomer may be characterized by the following chemical formula:

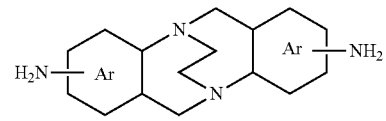

In an embodiment, the ethano-Tröger's base-diamine monomer may be characterized by the following chemical formula:

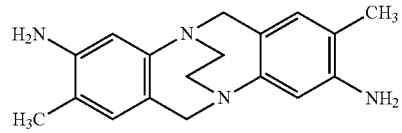

In an embodiment, the ethano-Tröger's base-diamine monomer may be characterized by the following chemical formula:

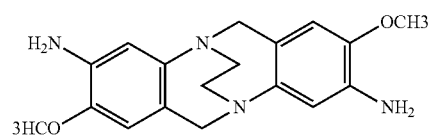

In an embodiment, the ethano-Tröger's base-diamine monomer may be characterized by the following chemical formula:

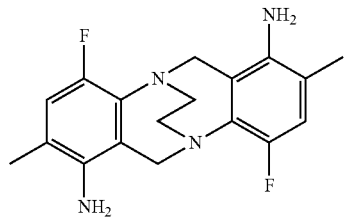

The anhydride monomer may include any anhydride, dianhydride, and/or multianhydride. In many embodiments, the anhydride monomer includes a tetracarboxylic dianhydride monomer. For example, the tetracarboxylic dianhydride monomer may be characterized by the following chemical formula:

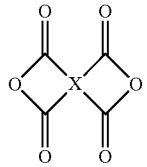

where X may be any tetravalent radical having an aromatic and/or aliphatic ring. For example, in many embodiments, X may be characterized by one or more of the following chemical structures:

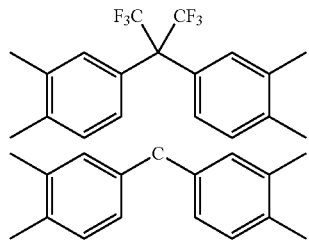

C = O, S, SO$_2$, CH$_2$, etc.

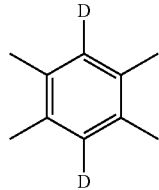

D = H, CH$_3$, C$_2$H$_5$, CF$_3$, etc.

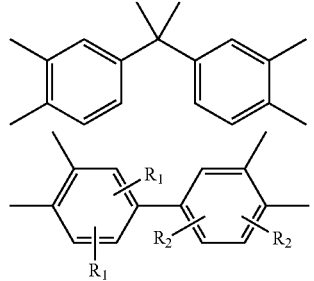

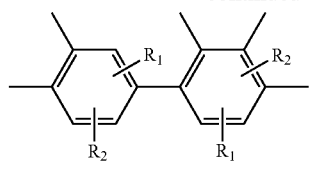

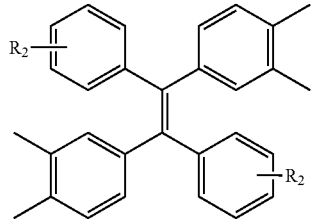

TPE

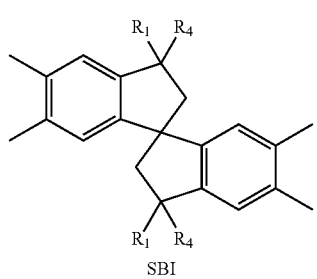

SBI

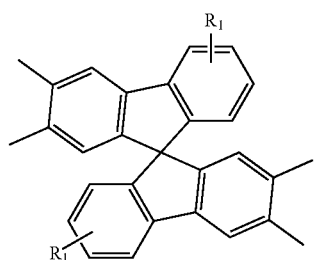

SBF

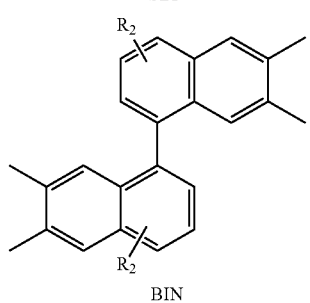

BIN

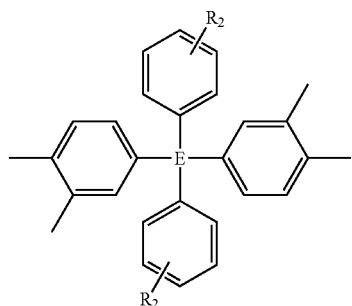

E = C, Si, et at.
TPM

-continued

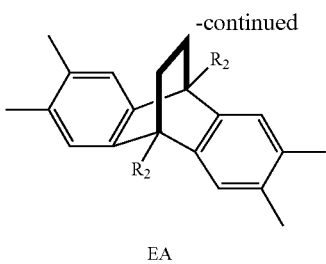

EA

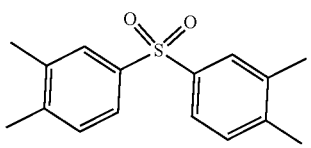

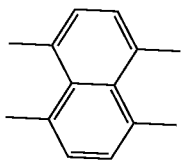

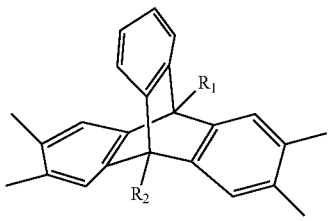

R, R₁, R₂ group 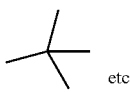 etc

-continued

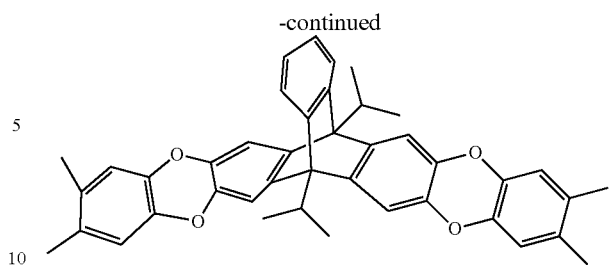

The solution may include a phenol containing a catalytic amount of an organic compound, wherein the organic compound includes at least one nitrogen. The phenol may include phenols and derivatives thereof. For example, in many embodiments, the phenol is a phenol derivative, such as m-cresol, and the phenol derivatives isomers, such as p-cresol and o-cresol. The organic compound containing at least one nitrogen may include a heterocyclic aromatic organic compound. In many embodiments, the organic compound containing at least one nitrogen is quinoline, as well as derivatives and isomers thereof. For example, the organic compound containing at least one nitrogen may be isoquinoline.

The step 302 is optional and may include precipitating the ethano-Tröger's base polyimide of intrinsic microporosity in a precipitating agent. For example, the ethano-Tröger's base polyimide of intrinsic microporosity may be precipitated in one or more of methanol and water, among other precipitating agents.

The ethano-Tröger's base polyimide of intrinsic microporosity prepared according to the method 300 may be characterized by the following chemical formula:

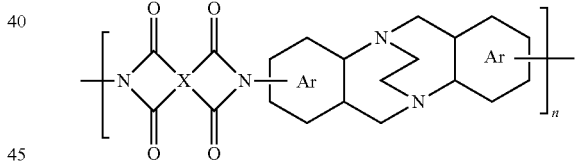

where Ar is an aryl group, n ranges from 2 to 10,000, and X is any tetravalent radical having an aromatic and/or aliphatic ring.

In an embodiment, an ethano-Tröger's base polyimide of intrinsic microporosity prepared according to the method 300 may be characterized by the following chemical formula:

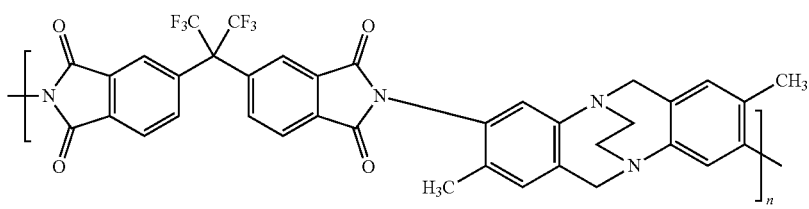

In an embodiment, an ethano-Tröger's base polyimide of intrinsic microporosity prepared according to the method 300 may be characterized by the following chemical formula:

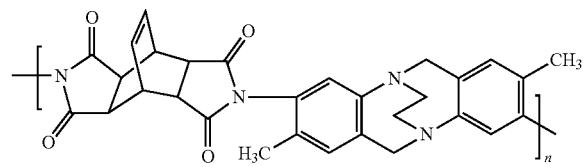

In an embodiment, an ethano-Tröger's base polyimide of intrinsic microporosity prepared according to the method 300 may be characterized by the following chemical formula:

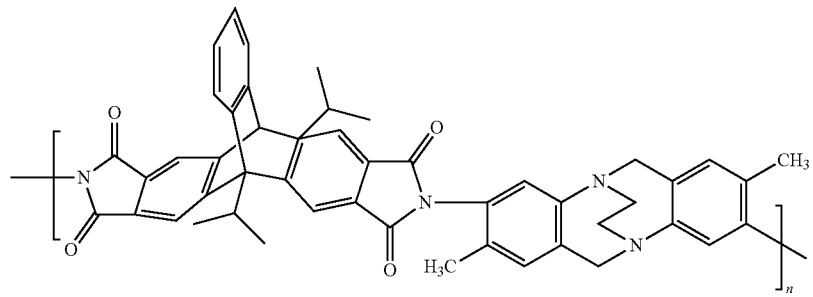

In an embodiment, an ethano-Tröger's base polyimide of intrinsic microporosity prepared according to the method 300 may be characterized by the following chemical formula:

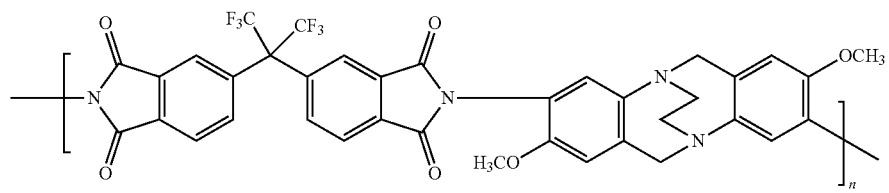

In an embodiment, an ethano-Tröger's base polyimide of intrinsic microporosity prepared according to the method 300 may be characterized by the following chemical formula:

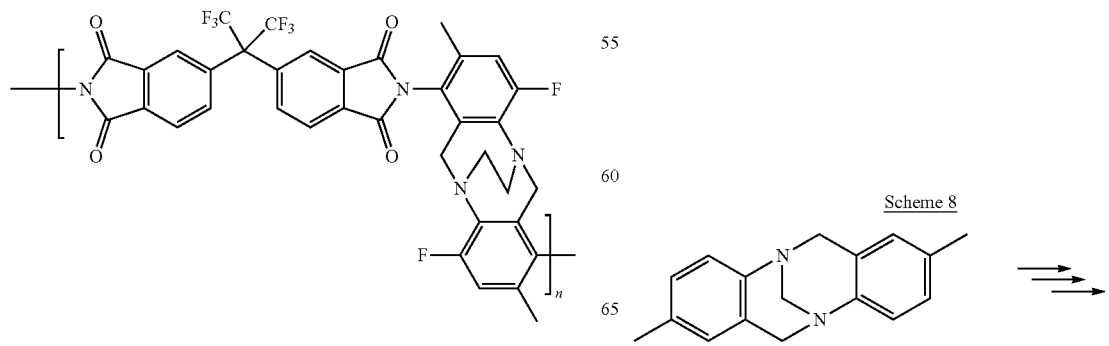

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

Example 1

To demonstrate the scope of the invention, three novel diamines represented by ETBDA 1, ETBDA 2 and ETBDA 3 were synthesized via a three-step synthetic route (Scheme 8). The parent compounds (ETB1, ETB2, and ETB3) were obtained by a direct alkylation reaction of 2,8-dimethyl-6,12-dihydro-5,11-methanodibenzo[b,f][1,5]diazocine; 2,8-dimethoxy-6,12-dihydro-5,11-methanodibenzo[b,f][1,5]diazocine; and 4,10-difluoro-2,8-dimethyl-6,12-dihydro-5,11-methanodibenzo[b,f][1,5]diazocine, respectively, followed by rearrangement of the resulting intermediate. Nitration of ETB compounds using potassium nitrate and concentrated sulfuric acid, followed by the reduction of the dinitro intermediate by palladium/C and hydrazine monohydrate afforded the diamine monomers. The molecular structures of all products and the three diamines were confirmed by $^1$H and $^{13}$C NMR, FTIR, and mass spectroscopic analysis.

Scheme 8

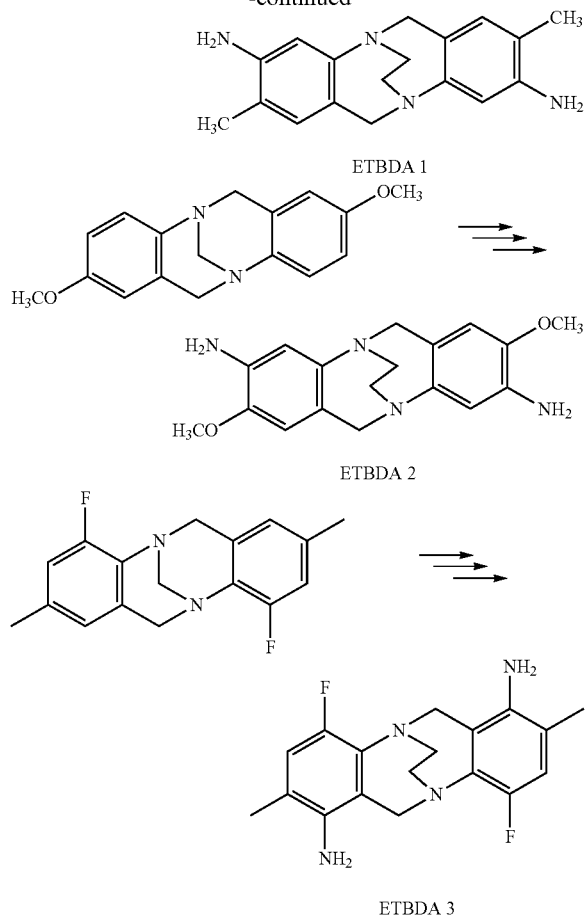

ETBDA 1

ETBDA 2

ETBDA 3

After purification and characterization, the three diamine monomers were polymerized with different tetracarboxylic dianhydride monomers to obtain high molecular weight ETB-PIM-PIs using a 1:1 molar ratio of dianhydride to diamine and the high-temperature, solution imidization method in m-cresol with catalytic amounts of isoquinoline.

All polymers exhibited high Brunauer-Emmett-Teller (BET) surface areas up to about 400 m² g⁻¹ (measured by nitrogen adsorption at about 77 K) and good solubility in organic solvents from which flexible and mechanically robust films were cast and used for gas separation performance testing.

The novel ETB-based polyimides exhibited excellent performance for a variety of important commercial gas separation applications, specifically $O_2/N_2$ and $CO_2/CH_4$ separation (see Table 1). For example, the polyimides according to Formulas 1-4 showed at least the same pure-gas $CO_2/CH_4$ selectivity as commercial cellulose for this separation. Importantly, the novel polymers of this Example showed about a 6- to 45-fold higher $CO_2$ permeability than cellulose triacetate ($P_{CO2}$=6.6 Barrer). Furthermore, compared to many other intrinsically microporous polymers, ETB-based polyimides demonstrated more stable permeation performance after aging for 70 days.

TABLE 1

Pure-Gas Permeation Properties of Various ETB-Derived Polyimides.

| Polymer | Sα (m²/g) | Pure-Gas Permeability (Barrer) | | | | | | Ideal Selectivity | | |
|---|---|---|---|---|---|---|---|---|---|---|
| | | He | $H_2$ | $N_2$ | $O_2$ | $CH_4$ | $CO_2$ | $O_2/N_2$ | $CO_2/CH_4$ | $H_2/N_2$ |
| FDA-ETB (Formula 1) | 124 | 88 | 92 | 1.91 | 9.38 | 1.11 | 41 | 4.9 | 37 | 48 |
| 6FDA-ETB (70 days aging) | | 84 | 88 | 1.44 | 8.27 | 0.86 | 38 | 5.7 | 44 | 61 |
| Bicyclo-ETB (Formula 2) | 157 | 162 | 279 | 6.0 | 31.9 | 5.5 | 155 | 5.3 | 28 | 24 |
| Trip-ETB (Formula 3) | 413 | 227 | 423 | 11.5 | 56.0 | 8.9 | 301 | 4.9 | 34 | 37 |
| 6FDA-ETB-DM (Formula 4) | | 217 | 283 | 10.2 | 50.9 | 9.0 | 281 | 5.0 | 31 | 28 |

1 Barrer = 1 × 10⁻¹⁰ cm³ (STP) cm cm⁻² s⁻¹ cmHg⁻¹

Formulas 1 to 4:

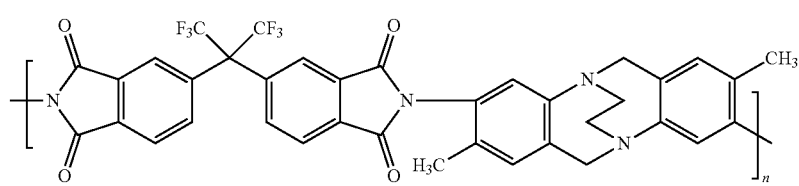

Formula 1

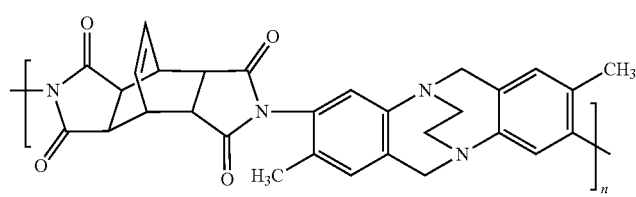

Formula 2

Formula 3

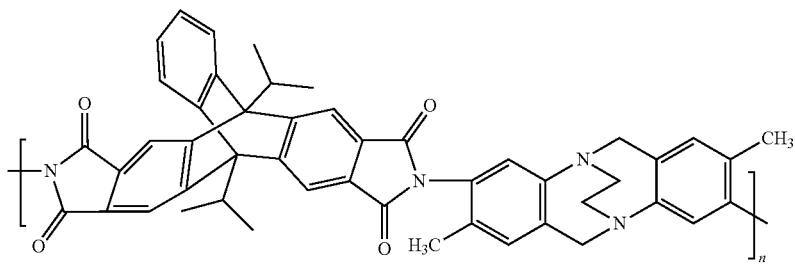

Formula 4

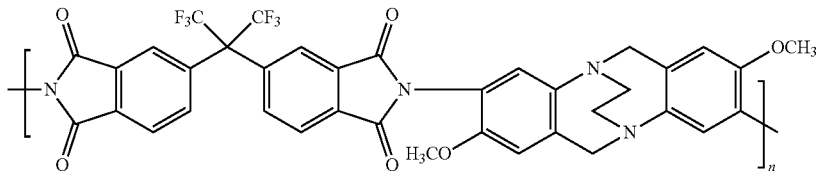

The polyimide according to Formula 5 also showed good gas permeation properties with $CO_2$ permeability of 773 barrer and $CO_2/CH_4$ selectivity of 18.

Formula 5

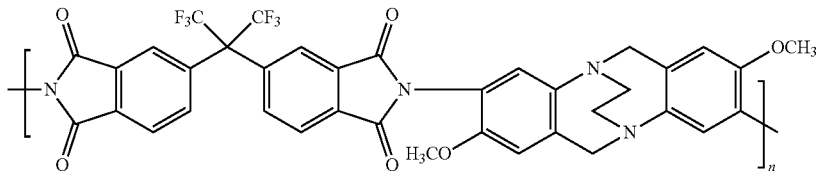

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A method of synthesizing an ethano-Tröger's base-diamine monomer, comprising:
   alkylating a Tröger's base to form a first intermediate compound including an ethano bridge;
   nitrating the first intermediate compound to form an intermediate dinitro compound including two nitro groups; and
   reducing each of the two nitro groups of the intermediate dinitro compound.

2. The method of claim 1, wherein the alkylating includes contacting a Tröger's base with an alkylating agent, and optionally one or more of a base and solvent.

3. The method of claim 1, wherein the Tröger's base includes Tröger's base derivatives.

4. The method of claim 1, wherein the first intermediate compound is characterized by the chemical formula:

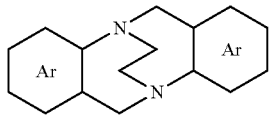

where Ar is one or more of a substituted aromatic benzene ring and unsubstituted aromatic benzene ring.

5. The method of claim 1, wherein the nitrating includes contacting the first intermediate compound with one or more of potassium nitrate ($KNO_3$), sulfuric acid ($H_2SO_4$), trifluoroacetic anhydride (TFAA), and nitric acid ($HNO_3$).

6. The method of claim 1, wherein the intermediate dinitro compound is characterized by the chemical formula:

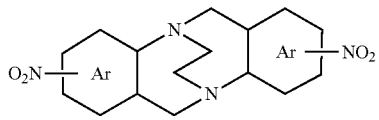

where Ar is one or more of a substituted aromatic benzene ring and unsubstituted aromatic benzene ring.

7. The method of claim 1, wherein the reducing includes replacing at least one of the nitro groups of the intermediate nitro compound with an amine using palladium/C and hydrazine.

8. The method of claim 1, wherein the ethano-Tröger's base-diamine monomer is characterized by the chemical formula:

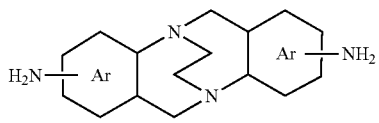

where Ar is one or more of a substituted aromatic benzene ring and unsubstituted aromatic benzene ring.

9. An ethano-Tröger's base microporous polyimide, comprising:

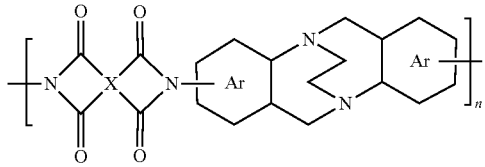

where X is a tetravalent radical having one or more of an aromatic ring and aliphatic ring, where Ar is one or more of a substituted aromatic benzene ring and non-substituted aromatic benzene ring, where n is 2 to 10,000.

10. The polyimide of claim 9, wherein X is characterized by one or more of the following chemical structures:

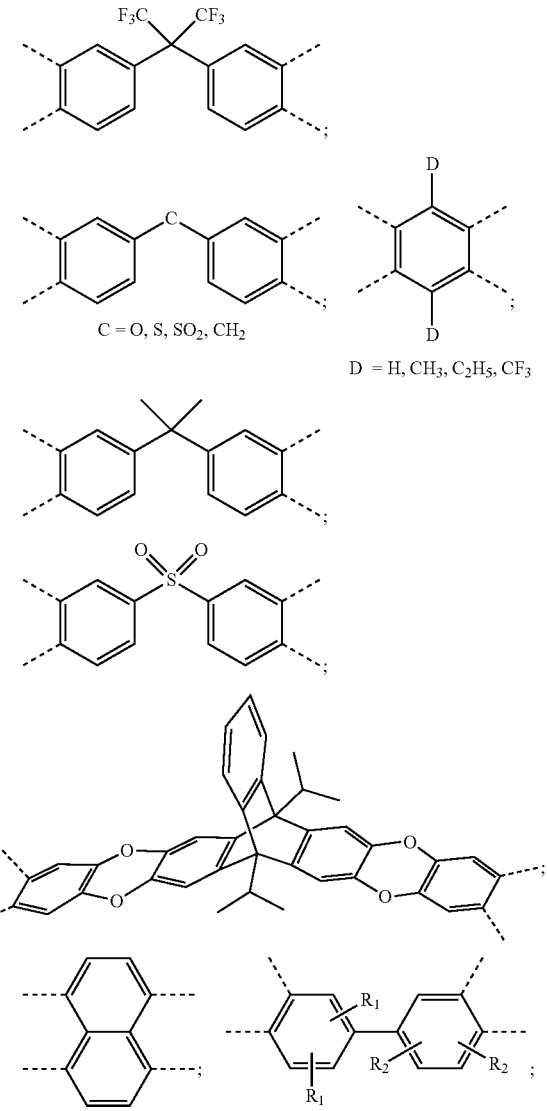

$C = O, S, SO_2, CH_2$ $D = H, CH_3, C_2H_5, CF_3$

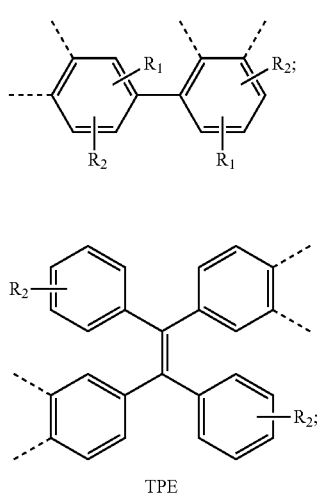

TPE

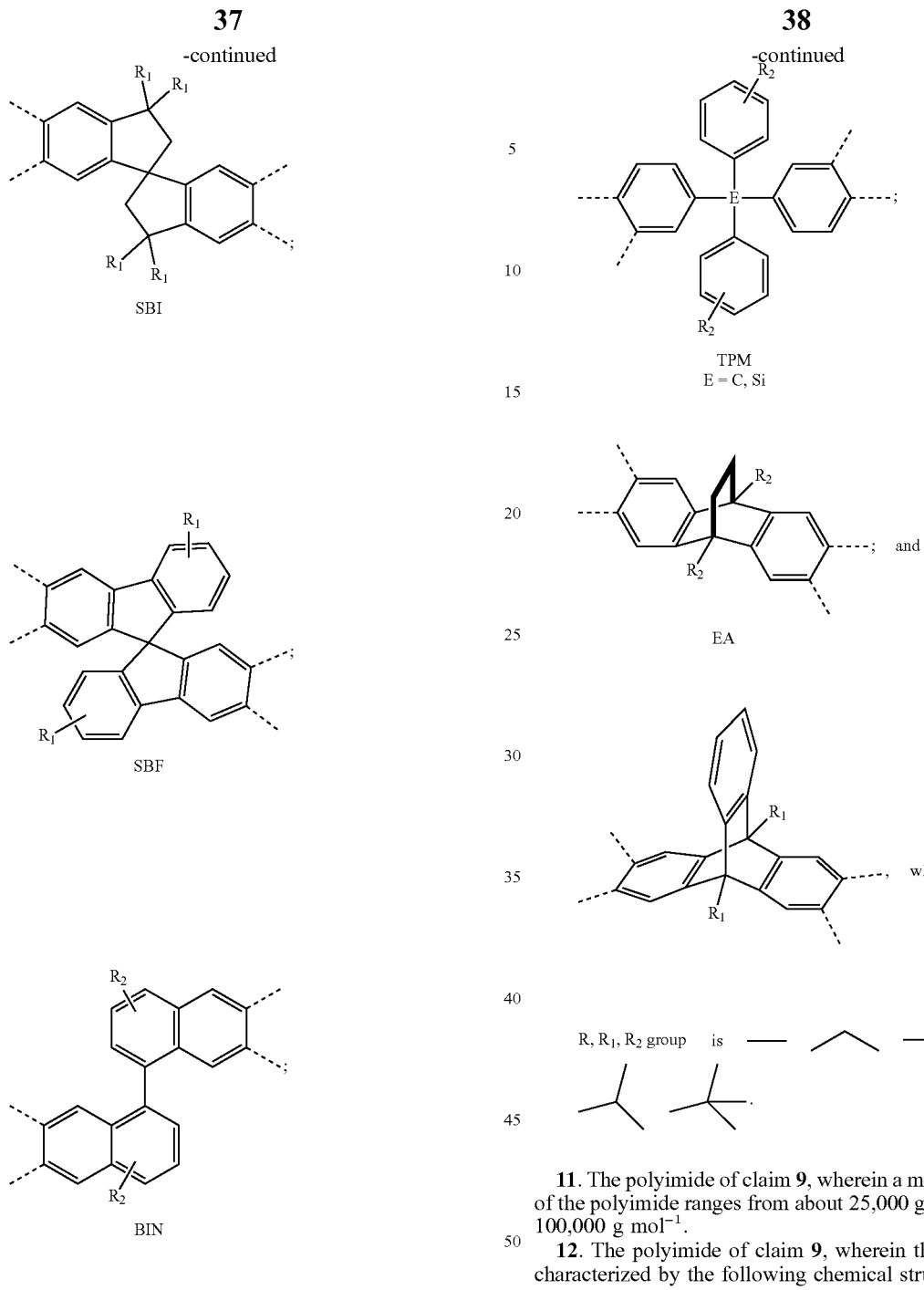
11. The polyimide of claim 9, wherein a molecular weight of the polyimide ranges from about 25,000 g mol$^{-1}$ to about 100,000 g mol$^{-1}$.
12. The polyimide of claim 9, wherein the polyimide is characterized by the following chemical structure:
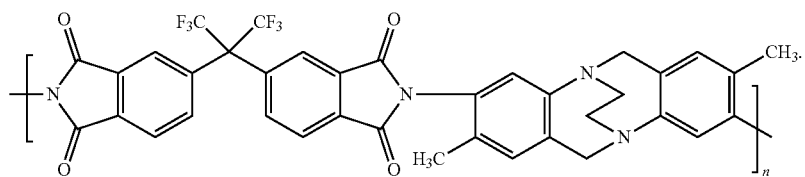

13. The polyimide of claim 9, wherein the polyimide is characterized by the following chemical structure:

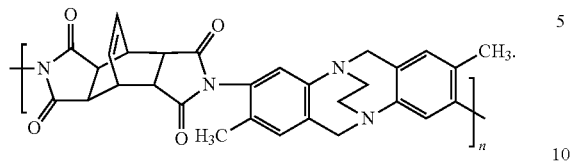

14. The polyimide of claim 9, wherein the polyimide is characterized by the following chemical structure:

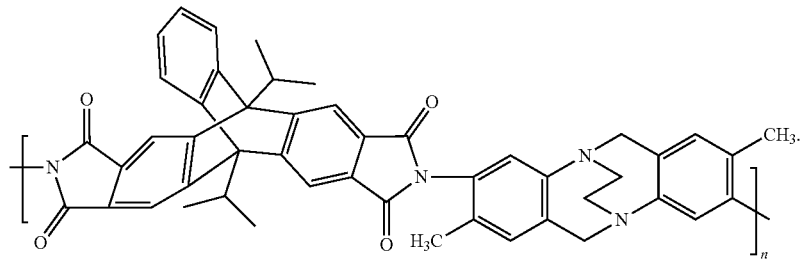

15. The polyimide of claim 9, wherein the polyimide is characterized by the following chemical structure:

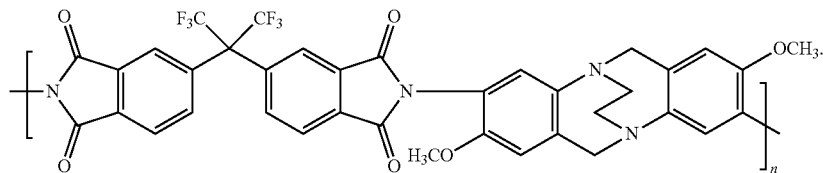

16. The polyimide of claim 9, wherein the polyimide is characterized by the following chemical structure:

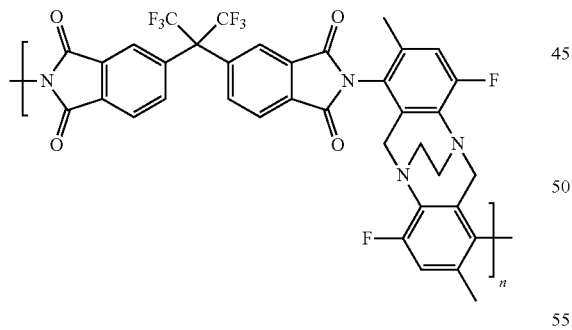

17. A method of separating chemical species in a fluid composition, comprising:

contacting a membrane based on an ethano-Tröger's base polyimide of intrinsic microporosity with a fluid composition containing at least two chemical species; and separating at least one of the chemical species from the fluid composition; wherein the ethano-Tröger's base polyimide of intrinsic microporosity is characterized by the chemical formula:

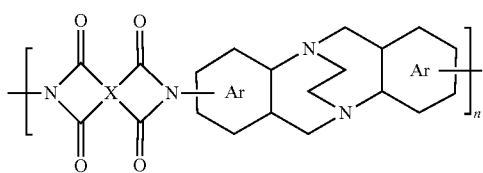

where X is a tetravalent radical having one or more of an aromatic ring and aliphatic ring, where Ar is one or more of a substituted aromatic benzene ring and non-substituted aromatic benzene ring, where n is 2 to 10,000.

18. The method of claim 17, wherein the fluid composition includes one or more of $O_2$, $N_2$, $H_2$, He, $CO_2$, $H_2S$, $C_{1+}$ hydrocarbons, olefins, paraffins, n-butane, iso-butane and butenes.

19. The method of claim 17, wherein X includes one or more of the following chemical structures:

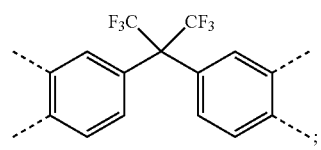

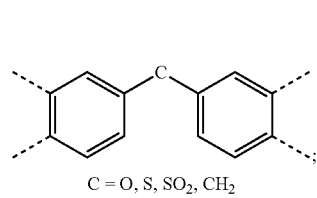 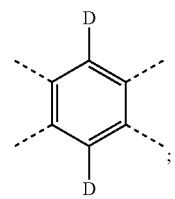

C = O, S, $SO_2$, $CH_2$

D = H, $CH_3$, $C_2H_5$, $CF_3$

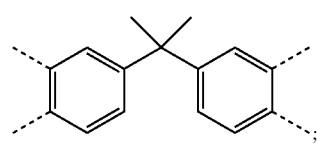

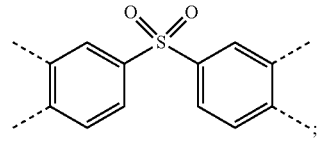

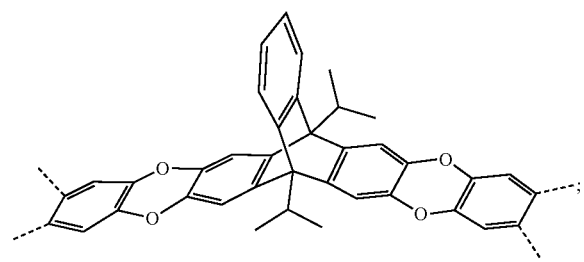

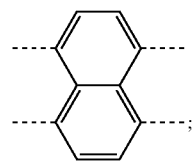 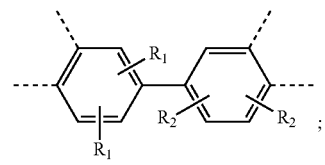

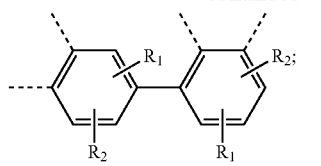

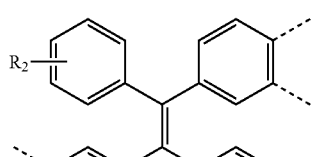

TPE

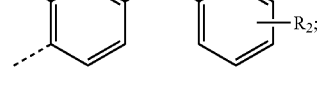

SBI

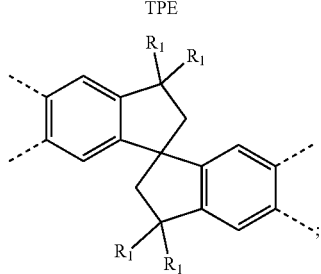

SBF

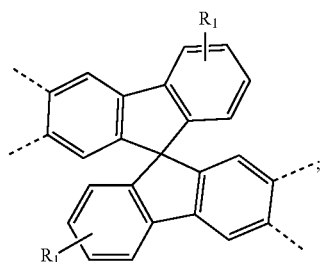

BIN

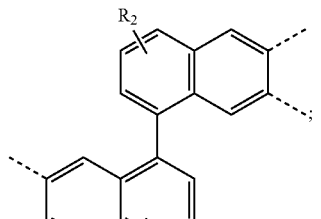

TPM
E = C, Si

-continued
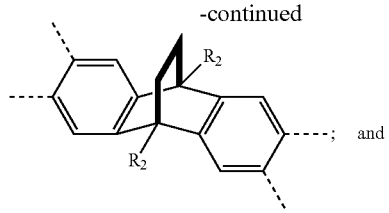
EA
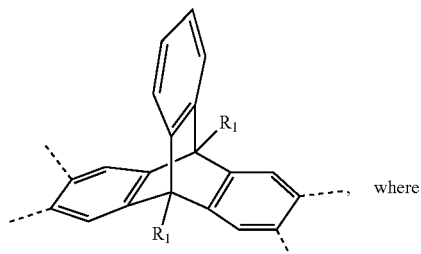
, where
R, R₁, R₂ group is 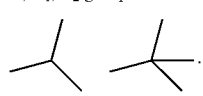 —$C_nH_{2n+1}$
20. The method of claim 17, wherein the at least one chemical species is $CO_2$, wherein the $CO_2$ is the at least one chemical species separated from the fluid composition.
* * * * *